(12) United States Patent
Nygard et al.

(10) Patent No.: US 6,590,215 B2
(45) Date of Patent: Jul. 8, 2003

(54) READOUT CIRCUIT FOR A CHARGE DETECTOR

(75) Inventors: Einar Nygard, Vettre (NO); Tsutomu Yamakawa, Tochigi (JP); Nobuyuki Nakamura, Tochigi-Ken (JP)

(73) Assignee: Toshiba Corporation, Tokyo (JP)

(*) Notice: Subject to any disclaimer, the term of this patent is extended or adjusted under 35 U.S.C. 154(b) by 124 days.

(21) Appl. No.: 09/827,439

(22) Filed: Apr. 5, 2001

(65) Prior Publication Data

US 2002/0145115 A1 Oct. 10, 2002

(51) Int. Cl.⁷ .............................. G01T 1/24
(52) U.S. Cl. ................... 250/370.09; 250/363.03
(58) Field of Search .................. 250/363.03, 370.09

(56) References Cited

U.S. PATENT DOCUMENTS

| | | | |
|---|---|---|---|
| 4,529,882 A | 7/1985 | Lee | 250/363 S |
| 5,619,040 A * | 4/1997 | Shapiro et al. | 250/370.09 |
| 5,656,818 A | 8/1997 | Nygård | 250/370.09 |
| 5,847,396 A | 12/1998 | Lingren et al. | 250/369 |
| 2001/0017352 A1 * | 8/2001 | Stark | 250/363.03 |

FOREIGN PATENT DOCUMENTS

EP    0 893 705 A2    1/1999

* cited by examiner

*Primary Examiner*—Constantine Hannaher
(74) *Attorney, Agent, or Firm*—Fitch, Even, Tabin & Flannery

(57) ABSTRACT

A method for detecting an active pixel in a sensor having a plurality of addressable pixels, comprising detecting a trigger event that causes a pixel to go active and setting a corresponding resettable latch from an initial unset logic state to a set logic state and establishing a time window during which another pixel which becomes active is assumed to originate from the same trigger event. For all pixels that become active within the time window a corresponding analog value of the pixel is sampled and held in response to a logic signal indicative of another pixel currently being active, and an incident time of the pixel going active is established. Each of the latches in the segment is sparsely read so as successively to identify latches which are in the set logic state each corresponding to an active pixel having a known address in the sensor segment. The known address of each active pixel is associated with the incident time of the pixel going active and the respective sampled and held analog value. The process is repeated respect of successive active pixels, after which the latches are reset.

29 Claims, 9 Drawing Sheets

READOUT CIRCUIT FOR A CHARGE DETECTOR

FIELD OF THE INVENTION

This invention relates to a charge detector for reading charge produced by an active pixel in the detector.

BACKGROUND OF THE INVENTION

A known diagnostic technique used in tomography for locating tumors involves injecting into a patient's bloodstream a radioactive isotope which targets the tumor, so that the location of the tumor can be derived by detecting the location of the radioactive isotope. Typically, the radioactive isotope emits γ-rays which are dispersed from the tumor site. In order to achieve the desired detection so as to determine the precise location of the tumor, it is necessary to image the patient's body in such a manner as to detect only those γ-rays which are emitted normally from the body and to ignore those γ-rays which are dispersed in other directions.

U.S. Pat. No. 5,656,818 (Nygard) assigned to the one of present applicants discloses such a radiation imaging system that includes a detector unit and a receiver unit. The detector unit includes a two-dimensional sensor, first and second amplifier channels, first and second multiplicity generators and first and second address generators. The two-dimensional sensor includes first and second sensing segments that sense radiation in a first direction and a second direction, respectively. Each first amplifier channel generates an output signal based on a detection output from a corresponding one of the first sensing segments. The first multiplicity generator generates a first multiplicity signal representing a number of the first amplifier channels generating output signals. The first address generator generates a first analog address of a first amplifier channel associated with a received output signal. The second amplifier channels, second multiplicity generator and second address generator operate in like manner with respect to the second sensing segments. The receiver unit includes converters for converting the first and second analog addresses into first and second digital addresses. The receiver unit also includes a tester for testing whether the first and second digital addresses represent a valid position address in the first and second direction based on the first and second multiplicity signals.

Different types of computer tomography are known in which such a radiation imaging system may be embodied. In Single Photon Emission Computed Tomography (SPECT) more than one detector is rotated around the subject. During the rotation of the detector, the counting of the gamma rays is repeated. Then, the radioisotope's distribution (tomographic image) is reconstructed based on the obtained count values of the γ-rays.

In contrast to SPECT where a radioisotope in the body emits γ-rays produced by a single photon, in Positron Emission Tomography (PET) a patient is administered a radioisotope that emits positrons (i.e. positively charged electrons). When the positrons meet electrons within the body, the positrons and electrons mutually annihilate and produce two γ-rays that propagate away from each other at an angle of 180° and are detected by respective detector segments in the PET scanner. The scanner's readout electronics record the detected γ-rays and map an image of the area where the radioisotope is located. Here also two simultaneous detections are indicative of a positron emission from the tumor site.

Thus, in PET two simultaneous γ-rays must be detected on opposite sides of the patient's body. The positrons are extremely short lived and simultaneity implies that the two γ-rays can both be detected within a short time window, which is 10 ns, for example. The PET scanner surrounds the patient like a CT scanner and typically comprises in the order of 200,000 pixels on two detector segments. Thus, it is necessary to detect two excited pixels within a short time difference and then to read out the energy of these two pixels. Only if the energy of each active pixel equals about 511 keV, (i.e. the energy of the incident γ-radiation) are the two photons the result of positron-electron annihilation and thus indicative of the tumor's location. Also in a PET scanner Compton scattering can occur within the detector, whereby a photon is only partially absorbed by the pixel and partially scattered to another pixel or occasionally to even more than a single pixel. In this case the sum of the energies of simultaneous active pixels will be equal to about 511 keV.

Another apparatus used for nuclear imaging is the Compton Camera. In the Compton Camera in order to determine the location of the γ-ray based on the detection of the single photon thus emitted, it is necessary that Compton scattering occur, so that another photon will be emitted substantially simultaneously, thereby allowing the angle of the incident γ-ray to be calculated.

Here, too, it is necessary to establish simultaneity of a γ-ray striking multiple pixels, although Compton Camera and PET must detect simultaneous γ-rays and so the time difference for establishing simultaneity of two or more pixels becoming active is more critical than SPECT. Known architectures for PET scanners use sequential readout whereby each pixel is read sequentially in order to determine whether or not it is active.

In EP 893 705 published on Jan. 27, 1999 entitled "Multi-Channel Reading Circuit for Particle Detector" and assigned to one of the present applicants, there is described a method for reading an array of pixels in a 2-dimensional image sensor so as to reduce the time taken to detect a single "active" pixel. Specifically, it is proposed in EP 893 705 to group pixels into predefined groups or segments (typically associated with a single ASIC) and to read out the pixels of only those groups of pixels that are found to contain an active pixel. Such an approach is based on the principle that determination of an active group may be made quickly providing that, at this initial stage, it is not required to determine which specific pixel within the active group is itself active. Having thus established which groups of pixels are active, each pixel in the active group is then read sequentially.

Whilst this is suitable for SPECT, it is not suitable for PET principally due to the very high rate at which pixels are activated in a PET scanner owing to its absence of a collimator. As a result, there are too many active pixels to make it practical to provide a tradeoff between providing a large number of groups or segments each containing a sufficiently small number of pixels that sequential readout in each group can be achieved in reasonable time. Specifically, whilst it is theoretically possible to reduce the number of pixels in each group so that pixels in each group that become active simultaneously within the 10 ns time window can be determined, the number of A/D converters that would then be required to effect digital processing of the active pixels would, in practice, be prohibitive.

The reading circuit described in EP 893 705 uses two detectors so as to detect Compton scattering, requiring that data be read out in the first detector from a large number of addressable pixels along respective channels in order to detect which pixel is "active". This is done by first integrating the charge associated with each pixel using an integrator in the form of an operational transconductance amplifier having a feedback capacitor. The integrated charge pulse is then amplified and shaped and the resulting analog signal is sampled and held, allowing its magnitude to be measured. In order to measure the peak magnitude of the shaped signal, the shaped signal must be very accurately sampled at the peak value. This requires an accurate determination of the peak time that occurs a fixed time difference $t_p$ after the emission of charge by the excited pixel. The fixed time difference $t_p$ is a function of the RC time constant of the shaper circuit and is therefore known.

Thus, in order to know when to sample the integrated charge signal, the time of occurrence $t_o$ of each charge emission must itself be accurately determined. This having been done, all that is then necessary is to sample the held integrated charge sample at a time $t_p$. A reading system for reading out the charge signals must therefore generate an accurate trigger simultaneous with the occurrence of each charge emission.

Obviously, if during every scan of the composite image sensor, each pixel is read sequentially only one at a time, then the current scan in each segment can be terminated when an "active" pixel is detected assuming that only pixel in each segment can be active. However, it is impractical to read each pixel in such a manner because of the time overhead involved in addressing each pixel separately and downloading the pixel data along a dedicated channel for further processing.

The need to avoid sequential readout is addressed by U.S. Pat. No. 5,847,396 (Lingren et al.) assigned to Digirad Corporation, which discloses a high-energy photon imaging system comprising an imaging head that includes a detector having a plurality of detection modules. Each detection module comprises a plurality of detection elements fixed to a circuit carrier. The detection elements produce electrical pulses having amplitudes indicative of the magnitude of radiation absorbed by the detection elements. The circuit carrier includes channels for conditioning and processing the signals generated by corresponding detection elements. Each conditioning and processing channel stores the amplitudes of the detection element electrical pulses exceeding a predetermined threshold. The detection modules employ a fall-through circuit, which avoids the need for sequential readout and automatically finds only those detection elements whose stored pulse amplitude exceeds the threshold. The fall-through circuit searches for the next detection element and associated channel having a valid event, meaning that the detection element exhibits a pulse magnitude that exceeds a certain threshold.

Lingren et al. is directed to a γ-ray camera and imaging system where both planar and SPECT images may be obtained. It is not directed to a PET system. The distinction is significant. SPECT systems, by definition, produce only a single emission from each γ-ray. Tomography is used to determine from multiple emissions, each deriving from a different γ-ray striking the detector, the source of emission of the γ-rays, i.e. the location of the tumor. Since each γ-ray derives from only a single emission, all such emissions are valid, providing only that the corresponding pulse magnitude consequent to the emission exceeds the threshold. This is determined using a threshold comparator coupled to each detection element, such that the output of each threshold comparator establishes whether or not the event is "valid". It is important to note that the actual energy level of the detection element is unimportant: all that is relevant is that its energy level exceeds the threshold. Thus, once an event is established as being valid, the fall-through circuit merely ripples through the valid events quickly in order to determine which detection elements are "active". Specifically, once a detection element is established by the threshold comparator as being valid, no further information regarding that detection element is required in order to effect the subsequent stage of computer tomography.

All this is very far from the case in PET systems where the mere establishment that a pixel is active does not mean that the event giving rise to that pixel becoming active is "valid". In PET systems the time of emission is of vital importance since only those emissions which occur simultaneously are of interest and any pixels that become active even within so short a differential time such as 10 ns for example must be disregarded as PET-type emissions. Furthermore, each γ-ray emission deriving from mutual positron-electron annihilation has an energy of 511 KeV and thus the peak energy of each emission is best measured and used to establish validity of the emission as a PET event. Such establishment is further complicated by the fact even a γ-ray emission deriving from mutual positron-electron annihilation may give rise to Compton scattering on the detector, in which case the energy of an active pixel may be less than 511 KeV whilst still constituting a valid event since it can be mated with one or more counterpart emissions whose cumulative energy is equal to 511 KeV. Usually the active pixel having lowest energy is assumed to be the primary pixel first hit by the photon and the other pixel or pixels are ignored. For the sake of completeness, it has to be noted that Compton scattering at the detector can also occur between different detector segments of a multi-segment detector, albeit with much reduced probability. It is possible also in this case to sum the energies of simultaneous active pixels between detector segments so as to establish whether active pixels in adjacent detector segments result from Compton scattering at the detector. In fact, it is not essential to consider such emissions since tomography can still be performed using only that pixel information relating to direct PET-type emissions. However, this results in useful information being ignored and this, in turn, means that a greater number of actual direct PET-type emissions must be collected in order to be able to perform tomography accurately. The fact that more direct PET-type emissions must be collected means that the time taken to collect the requisite data is increased and this, of course, means that the patient is exposed to more irradiation, which is undesirable.

It is thus clear that the system described by Lingren et al. does not address the very specific requirements associated with PET systems, where validity of an active pixel cannot be established only on the basis of the energy level exceeding a threshold and simultaneity and actual energy level of the pixel must be established very quickly in order to establish validity.

Simultaneity of γ-ray stimulated emissions in two opposite detector segments of a PET camera is established by correlating events in the two detector segments in order to establish that they derive from positron-electron annihilation giving rise to two γ-rays. As noted above, this is done by establishing that the two events are substantially simultaneous. Moreover, accurate simultaneity of the two events can be determined accurately only if the γ-ray emission is measured fast. Use of a single filter having a slow time constant for shaping the data signal resulting from the γ-ray emission, whilst commonly used, detracts from the accuracy with which the peak time can be measured and this, in turn, reduces the accuracy with which simultaneity of corresponding events in two detectors can be established.

EP 893 705 proposes the use of a fast shaper for determining the initiation of a γ-ray emission so as to establish when a pixel becomes active, whereupon a slow shaper determines the peak time. As noted above, this is used within the readout circuit of a Compton camera. However, accurate determination of the initiation of a γ-ray emission by the fast shaper serves to allow accurate sampling of the energy profile filtered by the slow shaper and sampled and held for subsequent measurement. This is done by reading the energy profile a known time delay after establishing initiation of the γ-ray emission by the fast shaper.

It is specifically to be noted that EP 893 705 does not rely on the accurate measurement of time of emission in order to establish simultaneity of emissions. Rather this is determined using logic gates connected to different detector segments so that segments that contain active pixels simultaneously are identified. Associated with each detector are groups of pixels, each group containing a plurality of pixels. A logic level associated with each group of pixels indicates which group contains an active pixel. Thus, simultaneity of two events, deriving from Compton scattering of a single photon, results in two detectors being active and of two groups, one in each active detector, being active: all this being determined using logic gates in real time. Time stamps are associated with each pixel but it is specifically noted that these are not used to establish simultaneity of a charge emission from the first and second detectors. Rather, as is also explained, the time stamp identifies the time of emission of the active pixel for the sole purpose of measuring the peak value of the energy profile filtered by the slow shaper. This is done after establishing simultaneity of active pixels in the manner explained above.

In PET, owing to the fact that the double photon emission derives from mutual annihilation of a single positron with a single electron, only two simultaneous photon emissions are possible. In practice, such occurrence can only be determined retroactively by detecting multiple photon emissions, establishing simultaneity and accepting simultaneous emissions as due to PET only if the number of such emissions is less than a predetermined threshold, typically two. This implies that the actual time of emission must be measured and recorded for subsequent analysis and, of course, that the time must be measured extremely accurately and quickly in order to allow for subsequent accurate matching of simultaneous emissions.

It has further to be borne in mind that use of PET does not prevent the occurrence of other physical phenomena, which have no relevance to PET and must not be allowed to corrupt the simultaneity measurements. Thus, simultaneous emissions do not necessarily indicate positron-electron annihilation since they could be due to Compton scattering within the body of the patient, for example, giving rise to two simultaneous from the body. As against this, however, Compton scattering can occur at the detector. In this case, the multiple photon emissions actually derive from only a single photon emitted from the tumor site, giving rise to a secondary effect when the photon strikes the detector, since not all of its energy is given up. As noted above, Compton scattering results in two (or more) active pixels having a combined energy of 511 KeV allowing it to be determined whether multiple simultaneous events are due to Compton scattering at the detector. In this case they cannot be ignored and usually the active pixel having lower energy is assumed to be the primary pixel first hit by the photon and the other pixel or pixels are ignored. For the sake of completeness, it has to be noted that Compton scattering at the detector can also occur between different detector segments, albeit with much reduced probability. It is possible also in this case to sum the energies of simultaneous active pixels between detector segments so as to establish whether active pixels in adjacent detector segments result from Compton scattering at the detector.

In summary, Lingren et al. disclose the use of fall-through in a SPECT system but is not concerned with the time of a photon's emission. EP 893 705 discloses the use of a fast shaper for accurately determining an initiation of a photon emission but uses this only to know when to read the energy level as filtered by a slow shaper and held by a sample and hold circuit. Thus, neither of these references addresses the very specific and stringent requirements inherent in PET systems where validity of two simultaneous events amongst a vast number of pixels must be done fast and requires both accurate time stamping of the events and subsequent measurement of the pixel energy.

SUMMARY OF THE INVENTION

It is therefore an object of the invention to provide a reading circuit for reading one or more "active" pixels in a 2-dimensional image sensor having a plurality of pixels.

According to a broad aspect of the invention there is provided a method for detecting an active pixel in a sensor segment having a plurality of addressable pixels, the method comprising the steps of:

(a) for each trigger event that causes a pixel to go active, setting a corresponding resettable latch from an initial unset logic state to a set logic state and establishing a time window during which another pixel which becomes active in said sensor is assumed to originate from said trigger event, (b) for all pixels that become active within said time window:
   i) sampling and holding a corresponding analog value of the pixel in response to a logic signal indicative of another pixel currently being active,
   ii) establishing an incident time of the pixel going active,
   iii) sparsely reading each of the latches in said segment so as successively to identify latches which are in said set logic state each corresponding to an active pixel having a known address in said segment,
   iv) for each active pixel associating the known address thereof with the incident time of the pixel going active and the respective sampled and held analog value,
   v) repeating steps iii) and iv) in respect of successive active pixels, and
   vi) resetting said latches.

According to another aspect of the invention, there is provided a simultaneity detector for detecting simultaneously active pixels in a sensor having at least two addressable segments each containing a plurality of addressable pixels, the simultaneity detector comprising:
   a respective sample and hold unit coupled to each pixel in each of the segments, each for sampling and holding a corresponding analog value associated with the pixel,
   a respective resettable latch coupled to each of the sample and hold units for changing from an initial unset logic state to a set logic state when the corresponding pixel goes active thereby establishing a time window within which any other pixel that subsequently goes active is considered to be a simultaneously active pixel, a logic circuit coupled to all segments in the detector for detecting two simultaneous segments in each of which there exists at least one active pixel, a lookup table in each segment having a plurality of addressable locations each corresponding to a respective pixel in the respective segment and storing the known address of the respective pixel, an analog multiplexer in each segment having a plurality of addressable channels each coupled to a respective sample and hold unit in said segment for carrying the corresponding sampled and held value of the respective pixel, a sparse readout circuit in each segment coupled to each of the latches in the respective segment for sparsely reading each of the latches therein so as successively to identify latches which are in said set logic state each corresponding to an active pixel having a known address in the respective segment, said sparse readout circuit being responsive to each of the set latches in turn for pointing successively to an addressable location in said lookup table so as to read the known address of the corresponding active pixel, and for addressing a corresponding channel of the analog multiplexer so as to derive the respective analog value of the corresponding active pixel, and a reset unit coupled to each of the latches in the respective segment for resetting said latches at a termination of said time window or within said time window if no simultaneous segments are detected.

In accordance with another aspect of the invention, there is provided a method for reading an analog data signal emitted by an active pixel in a sensor having a plurality of addressable pixels, the method comprising the steps of:

(a) converting the analog data signal associated with the active pixel to a digital signal having a first logic state and converting corresponding analog data signals associated with inactive pixels in the sensor to corresponding digital signals each having a second opposite logic state, (b) using said digital signals to identify the active pixel, and (c) reading a magnitude of the analog data signal in respect of said active pixel.

According to a preferred embodiment, each of the latches comprises a Flip Flop that is set to HIGH when the corresponding pixel is "active" and otherwise remains LOW. There is thus provided a bank of Flip Flops mapping the pixels in the sensor. However, whilst each of the active pixels in the pixel array has associated therewith an analog energy value, each of the corresponding Flip Flops has associated therewith a digital value HIGH (logic "1") or LOW (logic "0") which is used to address a lookup table in which there is stored an address corresponding to each Flip Flop and thus to each pixel in the sensor. The location of a HIGH Flip Flop in the bank of Flips Flops thus maps the location of the corresponding active pixel in the sensor and can be fed to an N-to-1 analog multiplexer having N inputs corresponding to N pixels and a single output channel for selecting the pixel corresponding to the active input. Thus, in the event of simultaneous emissions from more than one pixel, more than one Flip Flop will be HIGH although the energy values associated with the active pixels is still not known. The energy values of active pixels are determined using a fast shaper to capture the time of the peak and a slow shaper to determine the peak accurately, as described in EP 893 705. However, in order to read out the energy values, it is first necessary to determine which pixels are active and, of course, to do this quickly. In the invention, this is accomplished by using a sparse readout circuit to ripple through the Flip Flops and determine one by one which Flips Flops are HIGH. This can be done extremely quickly and as each HIGH Flip Flop is thus detected, corresponding to an active pixel, the address of the corresponding pixel is read from the lookup table and the corresponding energy value is accessed by the analog multiplexer. Such an approach obviates the need to read the pixels in the non-active groups, thereby saving considerable reading time.

Preferably, the analog value of the pixel is a first rising current pulse derived from an emission of electric charge consequent to the pixel being struck by a γ-ray. The current pulse is integrated by a preamplifier so as to produce an analog voltage step having a sharp change in level upon emission of the charge signal. The voltage step constitutes an initiation signal indicative of the time of emission $t_o$ and whose magnitude is proportional to the accumulated charge produced by the current pulse and which is collected by a feedback capacitor in the preamplifier. The reading circuit further includes at least one shaper in respect of each pixel in the active group which is responsive to the voltage step for amplifying and shaping the integrated charge in order to generate a slowly rising analog voltage signal having a high signal to noise ratio. An important feature of such an embodiment resides in the precision with which the shaped analog voltage signal is samples at its peak. Specifically, the reading circuit includes in respect of each pixel:

a fast shaper having a fast time constant coupled to the respective pixel for producing a timing pulse by fast shaping an output from said pixel, the timing pulse having a known relationship to an incident time of the respective pixel going active, a slow shaper having a slow time constant coupled to the respective pixel for simultaneously shaping the charge signal associated with the respective pixel so as to generate a slow response curve having high signal to noise ratio, a threshold discriminator for determining a time delay $\Delta t$ for the fast response curve to exceed said predetermined threshold, and sampling circuit for sampling the slow response curve at a further time interval $t_p - \Delta t$ where $t_p$ is the time at which the slow response curve reaches its peak value so as to sample the slow response curve substantially at its peak value.

BRIEF DESCRIPTION OF THE DRAWINGS

In order to understand the invention and see how the same may be carried out in practice, a preferred embodiment will now be described, by way of non-limiting example only, with reference to the accompanying drawings, in which.

DETAILED DESCRIPTION OF THE INVENTION

Figure 1:
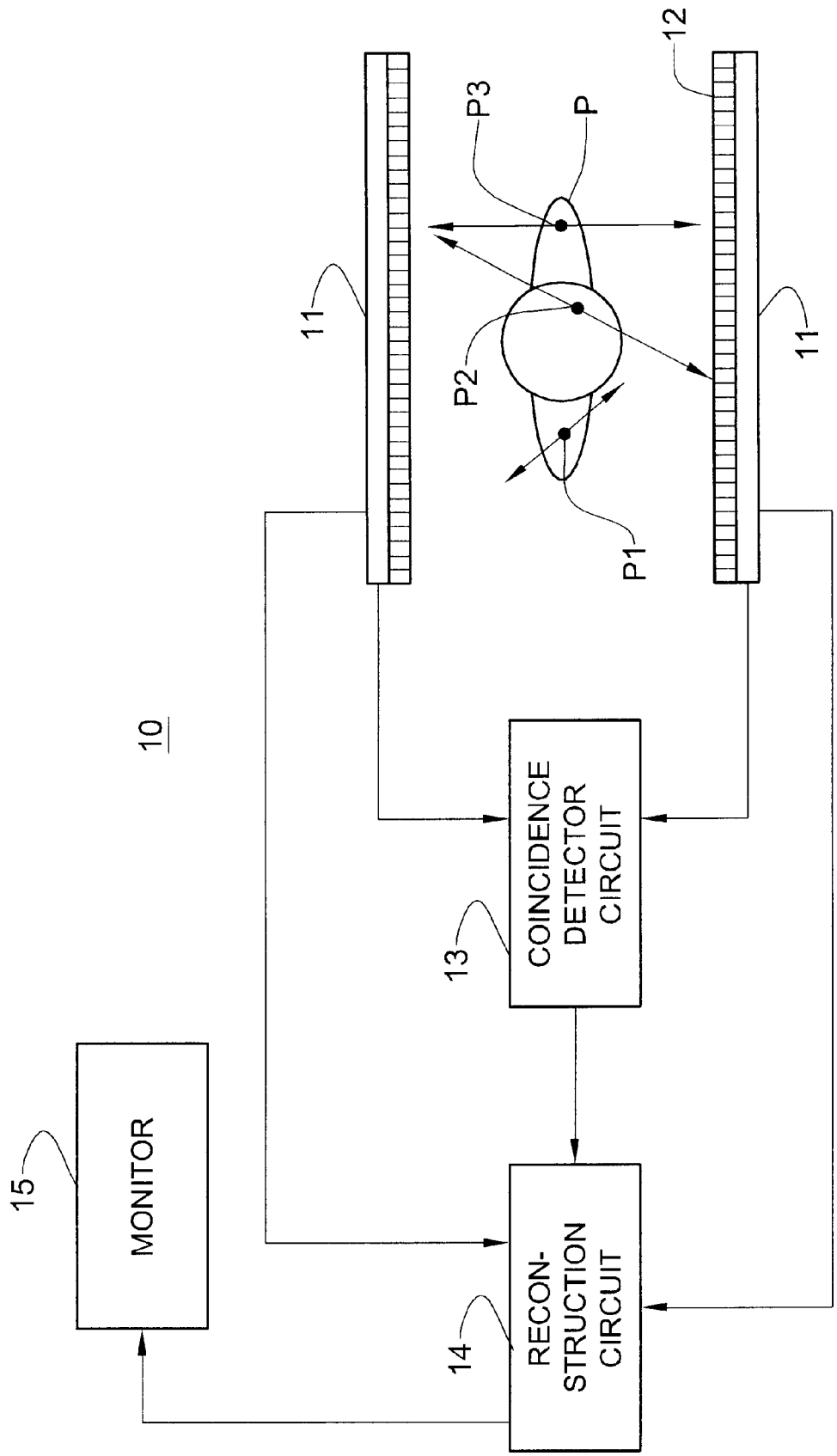
FIG. 1 is a schematic diagram showing a PET nuclear imaging system including a reading circuit for reading energy values and incident times associated with simultaneously active pixels in a sensor according to the invention.

FIG. 1 is a schematic diagram showing a PET nuclear imaging system depicted generally as 10 comprising a pair of detector segments 11 each having an array of 128 pixels 12 constituted by scintillators and photomultiplier tubes which are responsive to an incident γ-ray for producing a charge signal. By way of example, the detector segments 11 may be part of a PET scanner for use in computer tomography imaging of a patient's body. In such case, positrons shown as P1, P2 and P3 produced by a tumor site cause positron-electron annihilation resulting in the emission of two γ-rays that propagate away from each other at an angle of 180° and are detected by respective detector segments in the PET scanner. However, use of the invention is not limited to PET and can find application also for Compton Cameras, for SPECT and for conventional so-called Anger cameras. Coupled to the detector segments 11 is a coincidence detector circuit 13 whose output is fed to a reconstruction circuit 14, an output of which is fed to a monitor 15.

Figure 2:
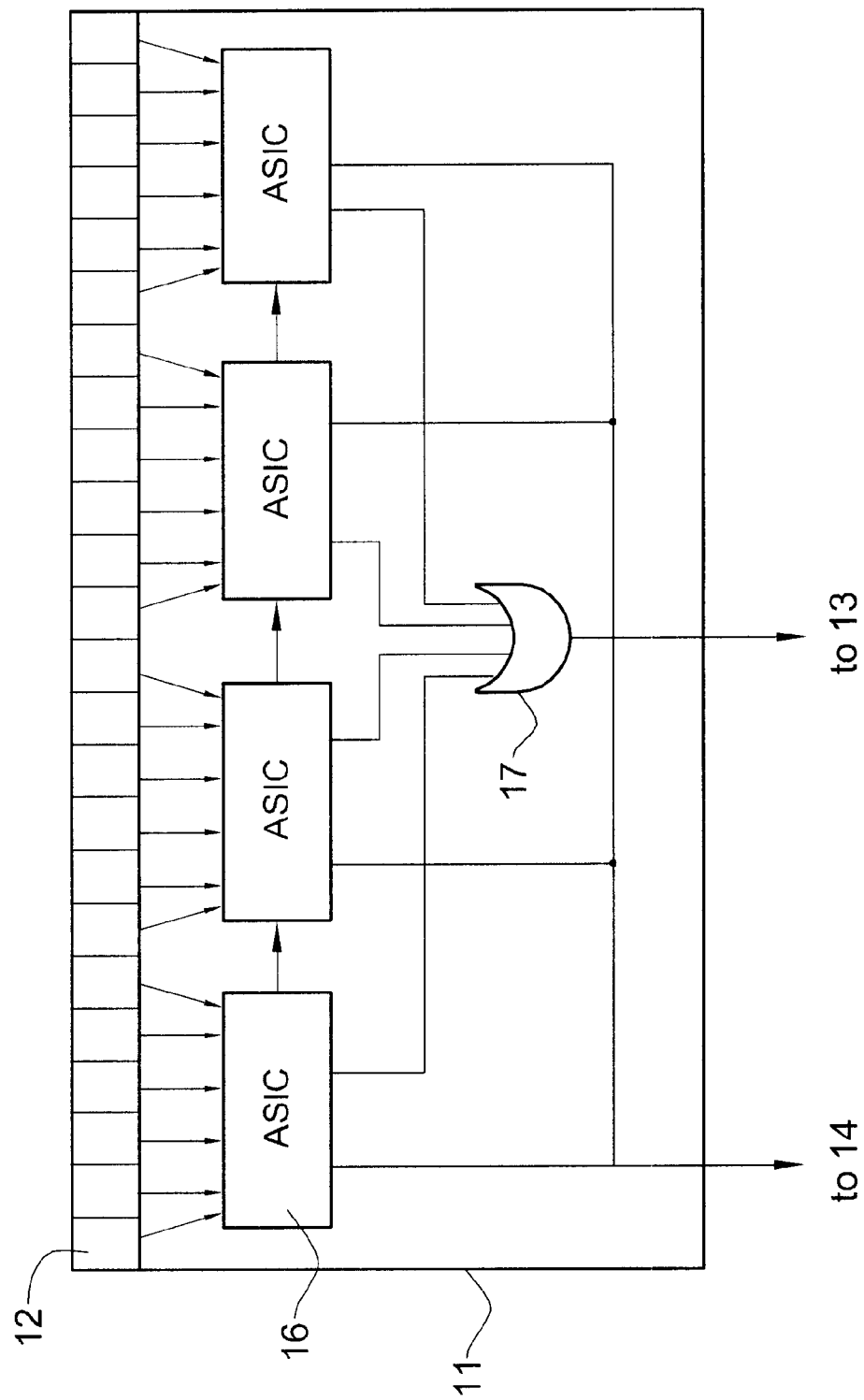
FIG. 2 is a schematic diagram showing a detector segment used in the nuclear imaging system of FIG. 1.

Details of the detector segments 11 will now be described with reference to FIGS. 2 to 6 of the drawings. FIG. 2 is a schematic diagram of the detector segment 11 connected to the pixels 12 and comprising a plurality of ASICs 16 and an OR-gate 17. The outputs of the pixels 12 are separated to some groups and fed to the ASICs 16 by the group. Each output of the ASICs 16 is connected to a respective input of the OR-gate 17.

All pixels 12 are connected to respective preamplifiers 20 whose outputs are fed to a respective fast shaper 22 for establishing an incident time of radiation striking the pixel and to a respective slow shaper 23 for determining the peak energy value of the pixel if it goes active. The respective output of each fast shaper is fed to a threshold discriminator 24 whose output is fed to a monostable 25. The outputs of the slow shapers 23 are read by respective sample and hold circuits 26 if activated by an external sample and hold signal 27. The monostables 25 are coupled to both a composite trigger unit 28 and to a sparse readout circuit 29. The outputs of the sample and hold circuits 26 are fed via a buffer 30 to the sparse readout circuit 29. The composite trigger unit 28 produces a trigger signal when any of the pixels in the respective channel goes "active". The output of composite trigger unit 28 goes high whenever one or more pixels is "active". A threshold level 32 is commonly fed to one input of all the threshold discriminators 24, whose outputs thus go "active" if the output of the corresponding fast shaper 22 exceeds the threshold level 32.

Figure 4:
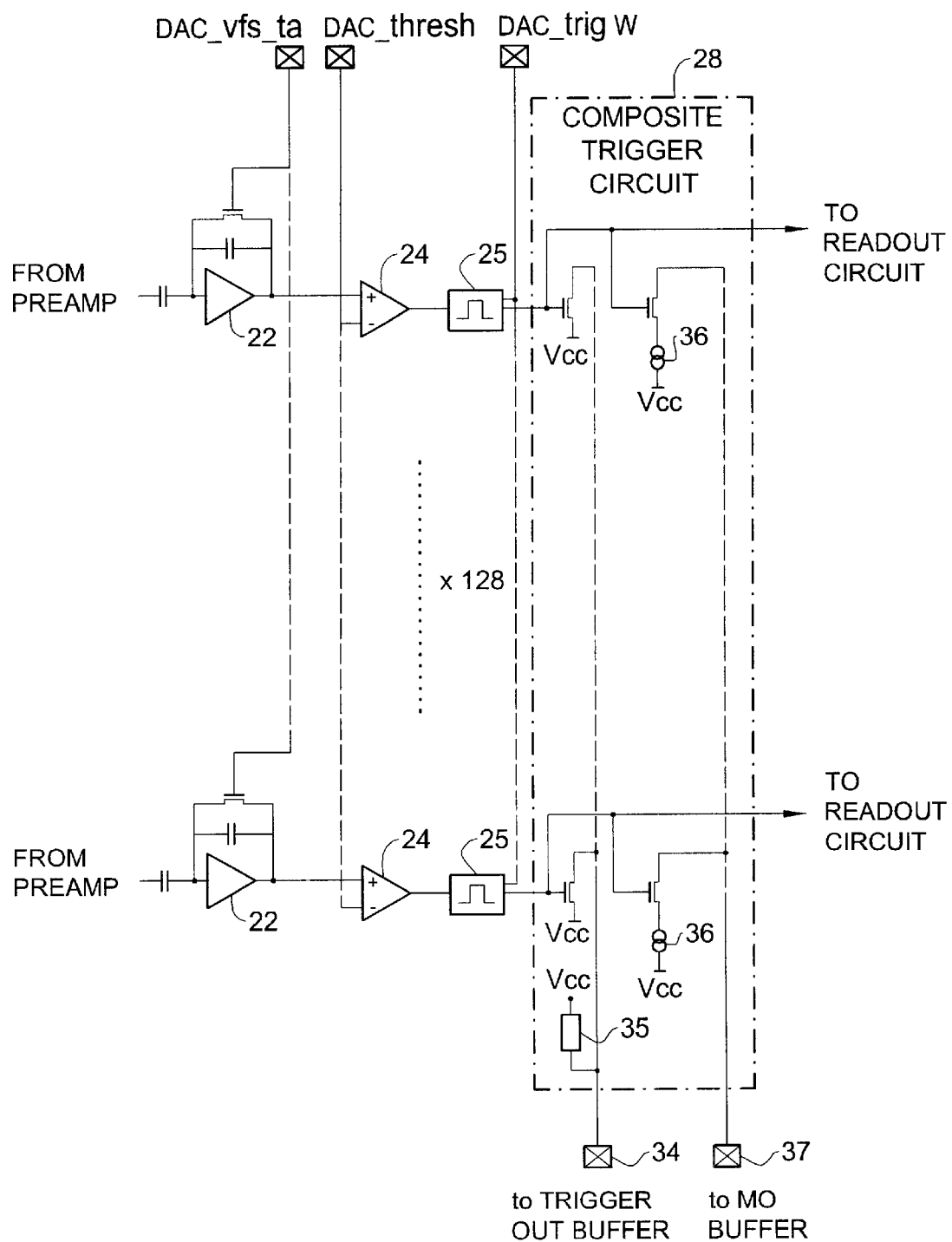
FIG. 4 is a schematic diagram showing a second partial detail of the reading circuit used in the nuclear imaging system of FIG. 1.
Figure 5:
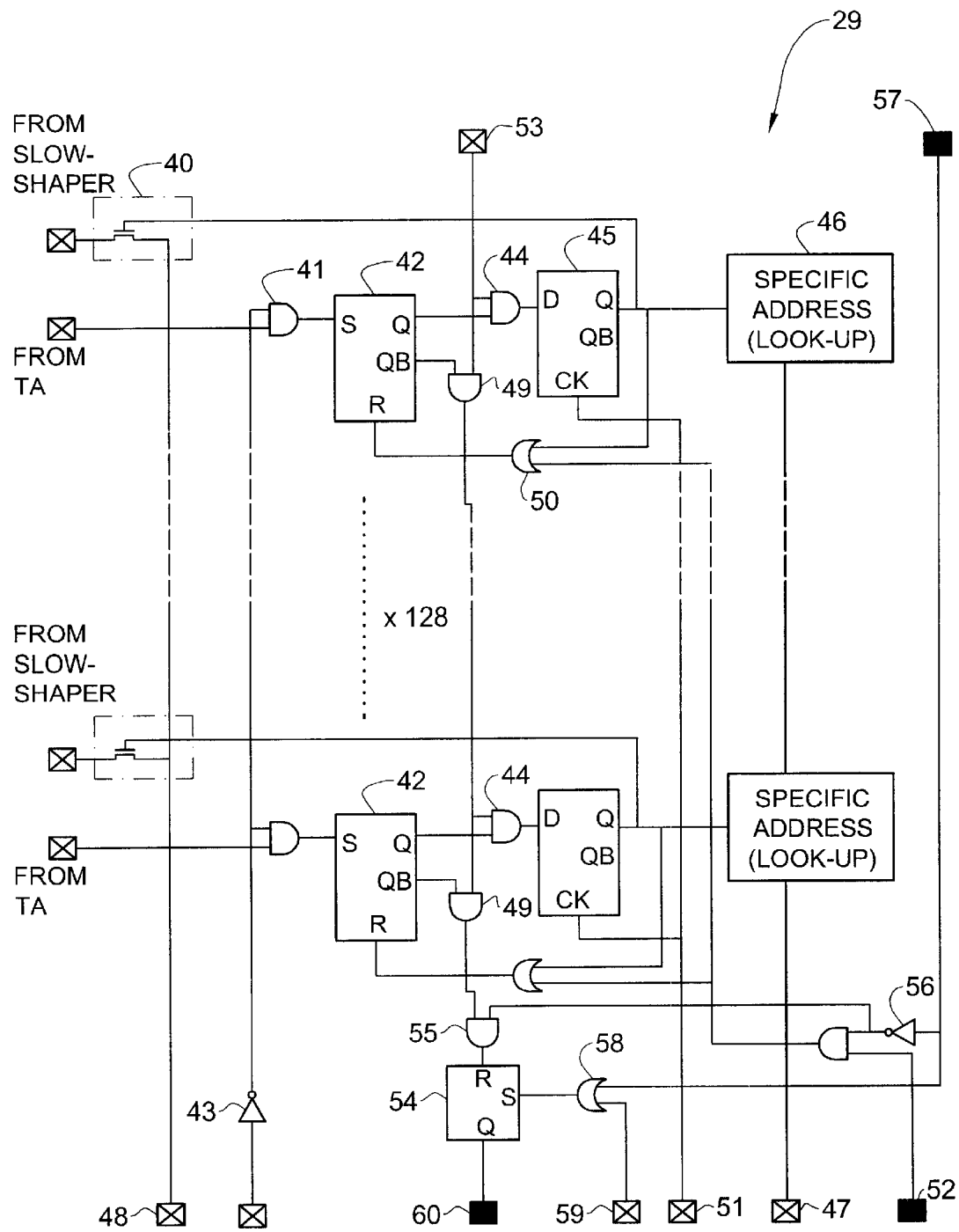
FIG. 5 is a schematic diagram showing a third partial detail of the reading circuit used in the nuclear imaging system of FIG. 1.
Figure 6:
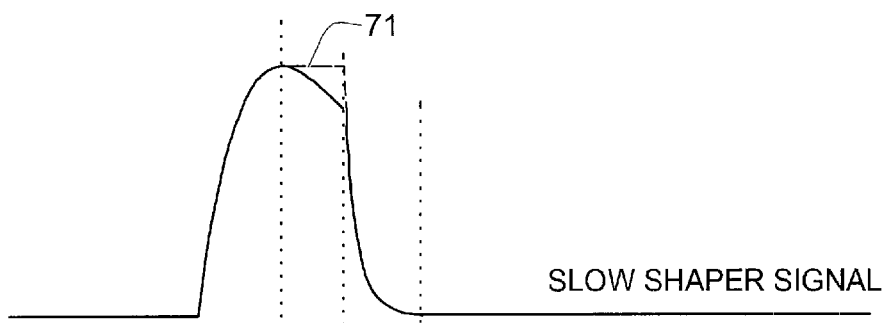
FIGS. 6a to 6d show graphically timing waveforms associated with fast and slow shapers used in the reading circuit of FIG. 3.
FIGS. 6e to 6g show graphically waveforms associated with a sparse readout circuit used in the reading circuit of FIG. 3.
Figure 6:
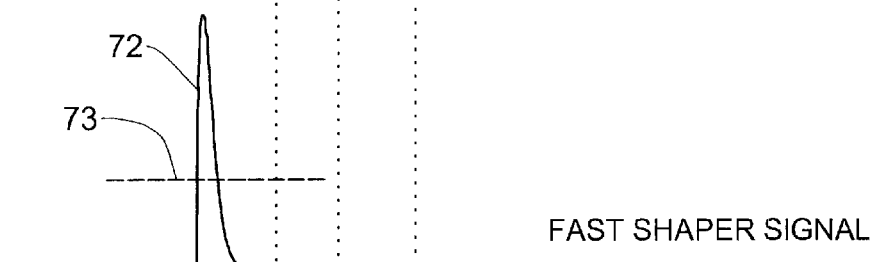
Figure 6:
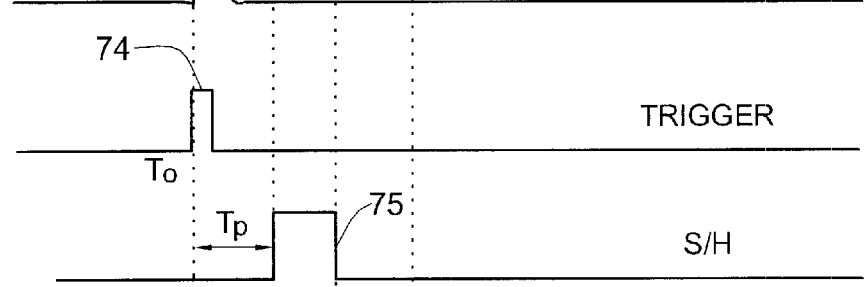
Figure 6:
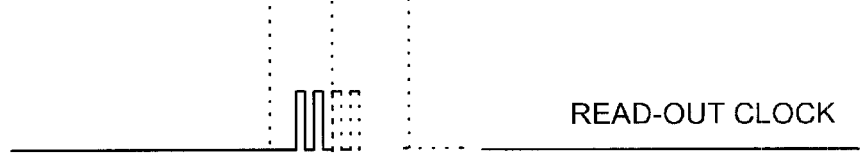
Figure 6:
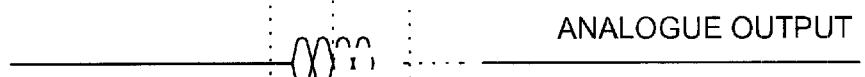
Figure 6:
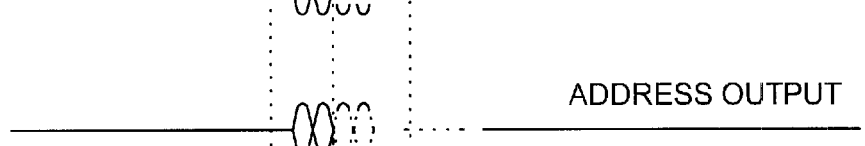

The principle of the composite trigger unit 28 is better shown in FIG. 4 from which it is seen that the outputs of the fast shapers 22 are fed to the respective threshold discriminator 24 whose output is fed to the mono-stable 25. The discriminator 24 outputs a signal if the output of the fast shaper 22 exceeds a predetermined threshold value, and the monostable 25 changes the signal from an initial unset logic state to a set logic state constituted by a pulse of predetermined period when the corresponding pixel goes active. This establishes a time window within which any other pixel in the same detector segment that subsequently goes active is considered to be a simultaneously active pixel. This will become significant if it transpires that two successive emissions within the time window correspond to Compton scattering of a γ-ray. In this case it may be possible to associate the original photon (usually having the lower energy value) with a simultaneous active pixel in the opposing detector segment. Respective outputs of the monostables 25 are wired OR-ed to produce the composite trigger output 34 that is HIGH if any one or more of the pixels is HIGH indicating that the corresponding ASIC 16 is "active". The wire OR-ed signal serves as a composite trigger signal 34 for the ASIC, such that if any pixel in the ASIC is "active" the composite trigger signal 34 will be HIGH and vice versa. Thus, if none of the pixels connected to the ASIC 16 is "active", then the composite trigger output 34 is LOW. The composite trigger output 34 is connected to the positive supply terminal Vcc via a pull-up resistor 35, so that it is HIGH until when any of the channels becomes "active", when it goes LOW. However, its state is inverted by an inverter (not shown) so that a HIGH output denotes an "active" channel. Clearly, all that is important is that its output changes state when a channel becomes "active" and it is a matter of design choice whether it goes HIGH or LOW. The composite trigger output 34 is used to generate a signal fed to the OR-gate 17 (shown in FIG. 2), the external sample and hold signal 27, and other signals including a ripple-signal 53 and a trigger signal 59 as indicated in FIG. 5. The PET nuclear imaging system 10 generates pairs of active pixels in respective opposing detector segments each of which detects a respective photon of a pair of photons emitted at an angle of 180° caused by mutual annihilation of a positron and an electron. The respective composite trigger outputs 34 are wired to the OR-gate 17 to produce a segment's trigger output. The trigger outputs of all the segments are logically AND-ed by the coincidence detector circuit 13 (shown in FIG. 1), which produces a high logic level if the trigger outputs of two or more segments are simultaneously "active". Coincidence detectors are known per se and so are not described in more detail. Consequently, an output of the coincidence detector circuit 13 constitutes a logic signal indicative of at least two pixels being active simultaneously. The coincidence detector thus allows simultaneity of charge emissions emanating from opposing detector segments to be established in real time. In practice, most charge emissions are not due to PET effects and an active pixel in one detector segment is not matched by a coincident active pixel in another detector segment. In this case, the sparse readout circuits 29 of the active detector segment are reset and the cycle starts again when a pixel goes active. The sparse readout circuit 29 is described below with reference to FIG. 4.

It will further be seen in FIG. 4 that the output of each monostable 25, as well as being wired OR-ed, is also fed to a respective current amplifier 36 that is triggered by the respective monostable 25. The output of each of the current amplifiers 36 is effectively wire-summed and fed to a Multiplicity Output 37. The Multiplicity Output 37 is used to generate a reset signal that resets the ASIC in a similar manner to the composite trigger output 34. The current amplifier 36 in combination with the Multiplicity Output 37 serves as a counter for counting a number of pixels producing charge signals on being hit by γ-rays. The resulting current is fed through a resistor so as to produce a voltage whose amplitude indicates how many channels were triggered. In PET it is necessary to detect at least two events from the opposing detector segments; however too many events may yield ambiguity in the measured position of the positron-electron annihilation. This serves for possible rejection of such events and for reset of the active detector segment. In practice, such rejection will be applied if more than three events are detected in an ASIC. It should be noted that the composite trigger signal 34 is not strictly needed because the Multiplicity Output 37 could be used for both chip-triggering and for determining the number of channels in the chip that triggered.

FIG. 5 shows a detail of the sparse readout circuit 29. The respective output of each sample and hold circuit 26 (shown in FIG. 3) is fed to a respective multiplexer cell 40. Each of the multiplexer cells 40 together constitutes an Analog Multiplexer. The trigger signal at the output of each of the monostable 25 is connected to a first input of a respective 2-input AND-gate 41 whose output is coupled to the Set-input S of a respective Set-Reset Flip Flop (SR Flip Flop) 42 (constituting a resettable latch), having Q and $\overline{Q}$ outputs. A logic signal DLT derived from the composite trigger output 34 is commonly fed to the respective second input of each of the AND-gates 41 via an inverter 43 and constitutes a Delay Late Trigger signal for preventing triggering of the SR Flip Flop 42 by another pixel becoming active in an unrelated event. Thus, for so long as DLT is LOW, each of the resettable latches will be set if the corresponding pixel is active. However, when DLT is set to HIGH, the latches are no longer set even if the corresponding pixel is active. The energy of such an unrelated pixel will still be sampled and held in the sample and hold circuit 26, but since the corresponding SR Flip Flop 42 is prevented by the DLT signal from being set, such an unrelated pixel will not be read out by the sparse readout circuit 29. The Q output of each SR Flip Flop 42 is fed to one input of a 2-input AND-gate 44 fed to the delay input D of a D-type Flip Flop 45 whose Q output is fed to an addressable memory 46, which stores the address of the respective pixel in the detector segment. The output of the addressable memory 46 is fed to the Reconstruction Circuit 14 (shown in FIG. 1) as an address signal 47. The Q output is also connected to the multiplexer cell 40 to have the output signal of the sample and hold circuit 26 fed to the Reconstruction Circuit 14 as an energy signal 48. The $\overline{Q}$ output of the SR Flip Flop 42 is fed to a second 2-input AND-gate 49 whose output is fed to an input of the corresponding adjacent second 2-input AND-gate 49 in the chain and to the input of the corresponding AND-gate 44 to whose other input the Q output of the SR Flip Flop 42 is connected. The Reset-input R of each SR Flip Flop 42 is triggered by the output of a respective 2-input OR-gate 50 one of whose inputs is connected to the Q output of the corresponding D-type Flip Flop 45 and whose other input is connected to a common reset line 51. A global clock signal 52 is commonly fed to the clock input CK of all of the D-type Flip Flops 45, so as to feed the logic state of the D-input of each D-type Flip Flop 45 to the Q-output thereof.

If a pixel is active, the composite trigger output 34 is generated in the composite trigger circuit 28 (shown in FIGS. 3 and 4), DLT goes LOW, and the corresponding SR Flip Flop 42 is set such that its Q output is HIGH and its $\overline{Q}$ output is LOW (until DLT goes HIGH and blocks any subsequent triggers). Each SR Flip Flop 42 that is set thus relates to a pixel that is active and whose energy value is held by the sample and hold output of the corresponding slow shaper 23 (shown in FIG. 3). The composite trigger output 34 is used as a reference timing signal for the readout process to enable sampling of the sample and hold circuits 26 at the correct time and to initiate the ripple-signal 53 that is applied from the top channel, and ripples through each channel until it arrives at a channel where the SR Flip Flop 42 is set HIGH. It will then stop because the $\overline{Q}$ output of the corresponding SR Flip Flop 42 is LOW and therefore the output of the AND-gate 49 is also LOW.

When the first readout clock-pulse 52 is then applied, the ripple-signal 53 together with the HIGH channel signal will be clocked to the output of the corresponding D-type Flip Flop 45. The clock signal 52 is fed to all the channels, but only one channel will be both HIGH at the same time as the ripple-signal is applied, so that of all triggered channels in the chip, only one will feed through to the output of the D-type Flip Flop 45. The output of this D-type Flip Flop 45 is now used to point out the channel address. At the same time the output of this D-type Flip Flop 45 is fed to the multiplexer cell 40 and switches it ON, whereby the output signal of the sample and hold circuit 26 is conducted through the multiplexer cell 40 as the energy signal 48. This means, as soon as the signal (based on the clock, ripple-signal and channel HIGH signal) goes through, the address and the energy will appear on the corresponding chip's output buses as the address signal 47 and the energy signal 48 respectively. The clock pulse is of sufficient period that during a single clock pulse, the ripple-signal 53 continues on its way down the channels to find and stop at the next SR Flip Flop 42 whose Q output is HIGH. Thus by the time the next clock pulse is applied to the D-type Flip Flop 45, the first SR Flip Flop 42 signal whose Q output is HIGH will be reset since the Q output of the corresponding D-type Flip Flop 45 is fed via the OR-gate 50 to the Reset-input R of the SR Flip Flop 42. This resets the SR Flip Flop 42, whose Q output thus goes LOW and whose $\overline{Q}$ output goes HIGH, thereby allowing the ripple signal 53 to ripple through to the next active channel. This process continues until the ripple-signal 53 reaches the bottom channel connected to a SR Flip Flop 54. The Reset-input R of the SR Flip Flop 54 is connected to a 2-input AND-gate 55, one input of which is coupled to the output of the last AND-gate 49 in the chain and the other input of which is coupled to the output of an inverter 56 to whose input is fed an active-indication signal 57. The Set-input S of the SR Flip Flop 54 is connected to a 2-input OR-gate 58, one input of which is coupled to a trigger signal 59 and the other input of which is coupled to the active-indication signal 57. When the output of the last AND-gate 49 goes LOW, it causes the Q output 60 of the SR Flip Flop 54 to go HIGH. This signal 60 is fed as the active-indication signal 57 to the next ASIC on the same detector segment 11. By such means, an "active" ASIC outputs a HIGH disabling signal 60 which fed to the next ASIC as the signal 57 thus disabling all of the other ASICs OFF as the clock signal 52 is shut down.

The ASICs operate as described above if there is coincidence. However, if the coincidence detector 13 detects that an active pixel has no coincident counterpart in the opposite detector segment 11, which means two (or more) composite trigger signals 34 are not fed to the coincidence detector 13 simultaneously, then a reset signal is applied to the common reset line 51 so as to reset all the SR Flip Flops 42 as well as the D-type Flip Flops 45.

Figure 3:
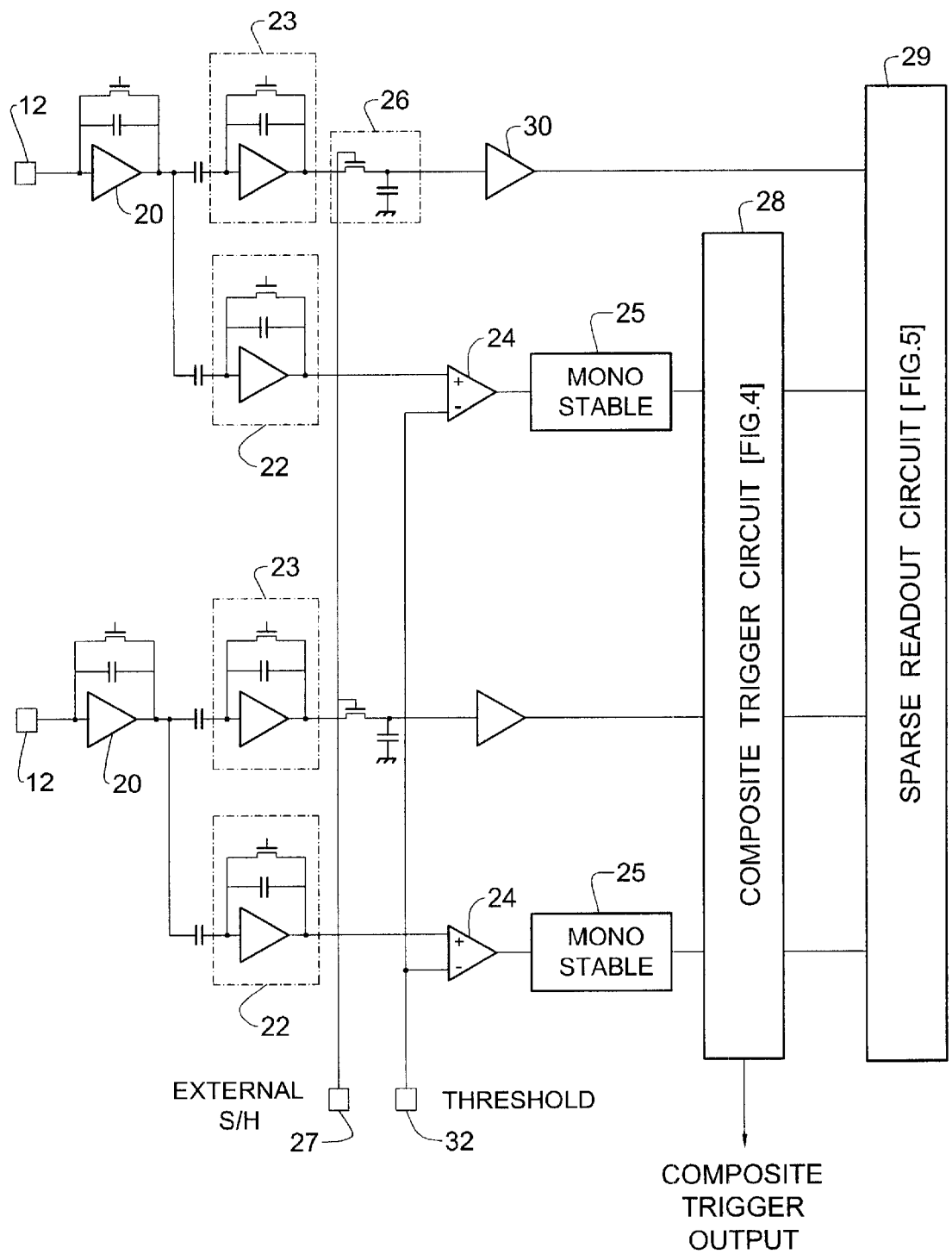
FIG. 3 is a schematic diagram showing a first partial detail of the reading circuit used in the nuclear imaging system of FIG. 1.

FIG. 6a shows graphically a signal waveform 70 which indicates the output of the slow shaper 23 and a signal level 71 denoting the output of the sample and hold circuit 26 and used to measure the peak energy level of the associated pixel. As explained above, this is done by measuring the value of the signal waveform 70 a time difference $T_p$ after the fast shaper signal 72 shown in FIG. 6b crosses the threshold 73. This generates a trigger pulse 74 shown in FIG. 6c establishing a time origin $T_o$. FIG. 6d shows a sample and hold pulse 75, which is shown in FIG. 3 as the external sample and hold signal 27 and is produced a time difference $T_p$ after the trigger pulse 74 for measuring the peak value of the slow shaper signal 70.

FIG. 6e shows graphically successive clock signals fed to the D-type Flip Flops 45 in the sparse readout circuit 29 and FIGS. 6f and 6g show graphically the respective address signal 47 and energy signal 48. It is thus shown that for each signal there is a corresponding energy value and address of an active pixel in the detector segment; there being no energy signal output in respect of inactive pixels. As a result, the active pixels are read out very quickly.

The time origin $T_o$ established by the fast shaper signal crossing the threshold 73 is, in fact, only an approximation of the time that a photon strikes an "active" pixel since it takes time, albeit very little, for the fast shaper signal 72 to cross the discrimination threshold 73. In fact, from a knowledge of the RC time constant of the fast shaper 22 and a knowledge of the level of the discrimination threshold 32, the time taken to cross the threshold 32 can be calculated and the time difference $T_p$ compensated for accordingly. Moreover, in practice, any slight error in determining the time origin $T_o$ of a photon striking an "active" pixel has little bearing on the accuracy with which the energy associated with that pixel is determined. This is because, the integrated charge signal stored in the sample and hold circuit 26 is shaped by the slow shaper 23 having a slow RC time constant and is relatively well spread out at the peak. Thus, a very small difference either side of the peak has negligible effect on the measured peak value.

However, any slight error in determining the time origin $T_o$ of a photon striking an "active" pixel does indeed have a critical bearing on the ability to determine whether two photons are simultaneous.

The difference in time taken for signals having a common time origin to pass the threshold is known as "time walk" and must be compensated for or eliminated in order to sample each of the signals at the correct time so as to obtain the respective peak value. Without such compensation, it is impossible to determine simultaneity of photon emissions. Furthermore, it is impossible to compensate for the delay between the time at which each curve passes through the threshold and the time at which the curve reaches its peak value and this impacts on the relative accuracy with which the peak values of different signals can be measured. Time-walk is illustrated graphically in FIGS. 7a and 7b, a possible original thereof will be explained with reference to FIG. 8 and a novel approach to its reduction will be described with reference to FIGS. 8, 9 and 10 of the drawings.

Figure 7A:
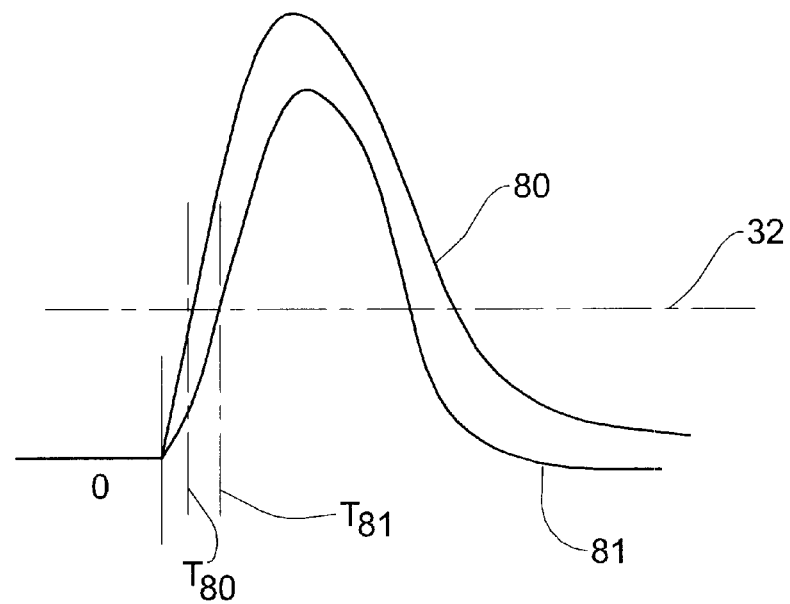
FIGS. 7a and 7b show graphically the effect of time walk in an integrated charge signal according to the "different energy" and "bulk" theories, respectively.

There are two theories of the cause of error made in determining the time origin $T_o$. One theory can be seen from FIG. 7a showing a pair of fast shaper signals 80 and 81 both emanating from a common absolute time origin O but having slightly different time derivatives and peak voltages. This is typically due to Compton scattering whereby an initial photon is partially absorbed by a first pixel, giving rise to the first signal 80, and partially scattered to another pixel giving rise to the second signal 81. In this case the sum of the energies of simultaneous active pixels is equal to 511 keV. As a result, the signal 80 crosses the threshold (shown in FIG. 3) at a time $T_{80}$, which is somewhat before the time $T_{81}$ when the signal 81 crosses the threshold 32 giving rise, in effect, to different time origins. The difference between the time $T_{80}$ and the time $T_{81}$ may well exceed 10 ns. In such case, the two signals 80 and 81 would be rejected as simultaneous even though, in fact, they are thus losing valuable data.

Figure 7B:
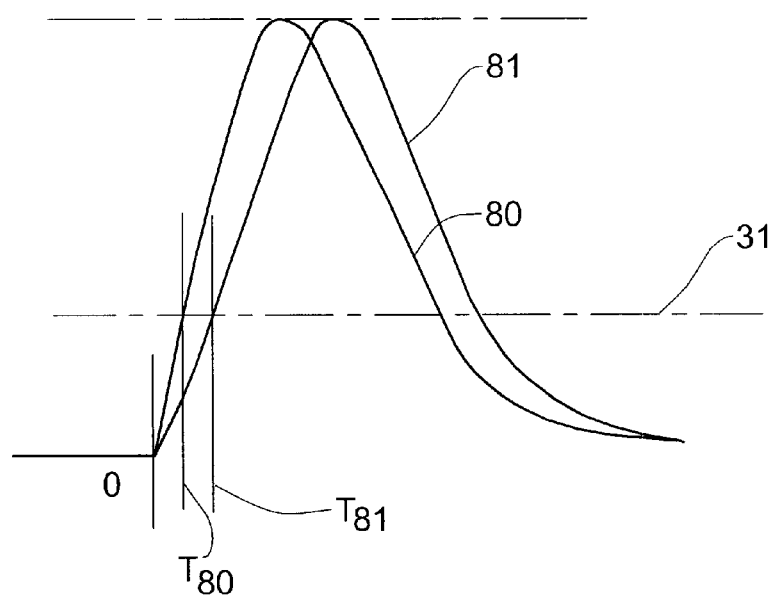

The other theory can be seen from FIG. 7b showing graphically the situation where the two signals 80 and 81 both emanate from a common absolute time origin O having slightly different time derivatives albeit identical peak energies. This is due to the so-called "bulk theory", described below with reference to FIG. 8.

Figure 8:
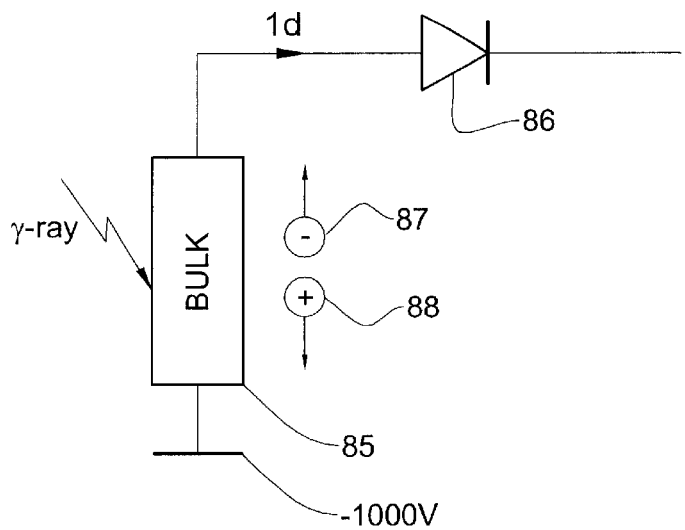
FIG. 8 shows schematically a pixel in a charge detector useful for explaining the origin of "time walk" associated with a signal detected thereby.

FIG. 8 shows schematically an equivalent circuit of a pixel having a semiconductor or scintillator bulk 85, for example silicon or CdTe as semiconductor or BGO as scintillator, one end of which is biased at a voltage of −10V using silicon or −1000V using CdTe and the other end of which is connected to an anode of a rectifier diode 86. When a γ-ray strikes the bulk, it releases an electron 87 from the bulk. The released electron 87 moves towards the anode of the rectifier diode 86, while the resulting positively charged hole 88 propagates towards the negatively charged end of the bulk. The total charge indicated by the maximum charge current that is created owing to a γ-ray striking the bulk is independent of where in the bulk the γ-ray strikes. However, the rate of change of charge current is a function of how fast the released electron reaches the diode 86 and this will be shorter for a γ-ray that strikes the bulk close to the diode 86 than for one that strikes remote therefrom. This difference in the rate of change of charge current is said to derive from "charge collection time" and is seen as a difference in the rate at which the charge current reaches its maximum level. Specifically, it gives rise to time walk whereby the time taken for the charge current to reach the threshold varies according to the rate at which the charge current crosses the threshold.

Thus reverting to FIG. 7b, a γ-ray that strikes the bulk close to the diode 86 would give rise to the signal 80, while the same γ-ray striking the bulk remote from the diode 86 would give rise to the signal 81. The time origin $T_o$ for these signals thus varies according to where in the bulk the γ-ray strikes the pixel. As noted above, the absolute times of photon emission are not known and are not important in this context since simultaneity between two emissions is determined by the measured time at which the respective signals reach the threshold. It is therefore important that the delay between the actual time of occurrence and the detection time be independent of the characteristics of the integrated charge signal.

Time walk may also arise from differences in the peak value $V_P$ of the signal, which affects the rate at which the integrated charge signal reaches the peak owing to the frequency characteristics of the fast shaper.

Figure 9:
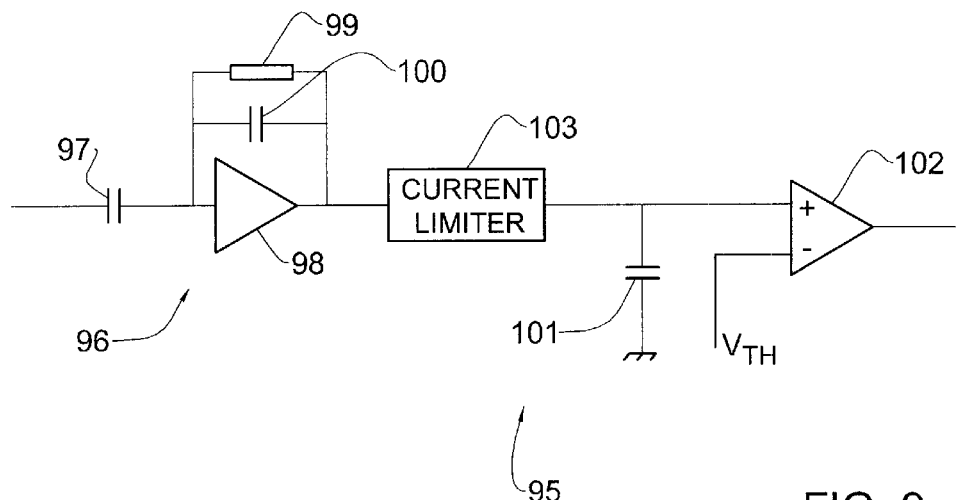
FIG. 9 is a schematic diagram showing a timing detector according to the invention including a modified fast shaper for shaping the integrated charge signal.

FIG. 9 shows a detail of a timing detector 95 comprising a fast shaper 96 having an input capacitor 97 for coupling to an amplified integrated charge signal. The fast shaper 96 includes an operational transconductance amplifier 98 having a fast RC time constant determined by a feedback resistor 99 and a feedback capacitor 100. The fast shaper 96 also includes an output capacitor 101 for accumulating voltage and which is connected to a threshold discriminator 102 for comparing the accumulated voltage across the output capacitor 101 with a fixed threshold, $V_{TH}$. Connected between the output of the amplifier 98 and the output capacitor 101 is a current limiter 103, which limits the current that can flow into the output capacitor 101 and thus the rate at which it saturates. In practice the current limiter 103 is realized by limiting the bias current of the output transistors within the amplifier so that they cannot sink current greater than a specified, reduced value. Clearly, this may be done by modifying the external bias resistors so that, for a MOSFET, the depletion layer is pinched thus allowing less current to pass therethrough.

Figure 10:
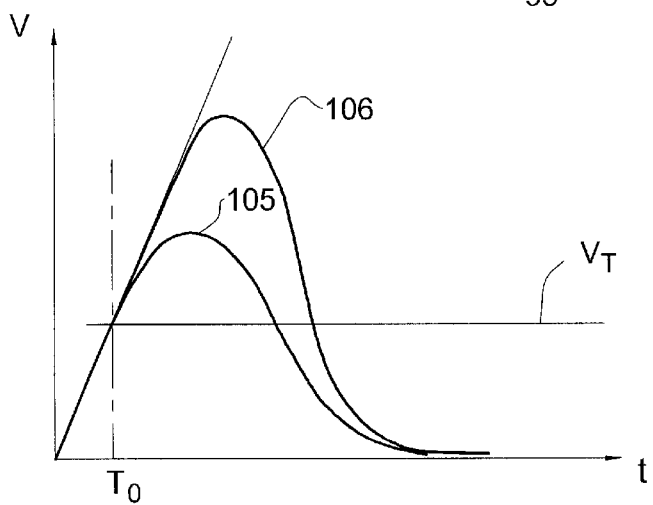
FIG. 10 shows graphically the effect of reduced time walk between a pair of signals discriminated by the timing detector shown in FIG. 8.

FIG. 10 shows graphically curves 105 and 106 representing charge current against time for two charge signals having different peak amplitudes. It is seen that both curves 105 and 106 are constrained to rise with the same slew rate, so that they reach the threshold $V_T$ is substantially at the same $T_o$. Therefore, the times at which the respective photon emissions are detected is independent of the peak amplitude of the integrated charge as well as where in the bulk the photon struck in order to trigger the event.

Figure 11:
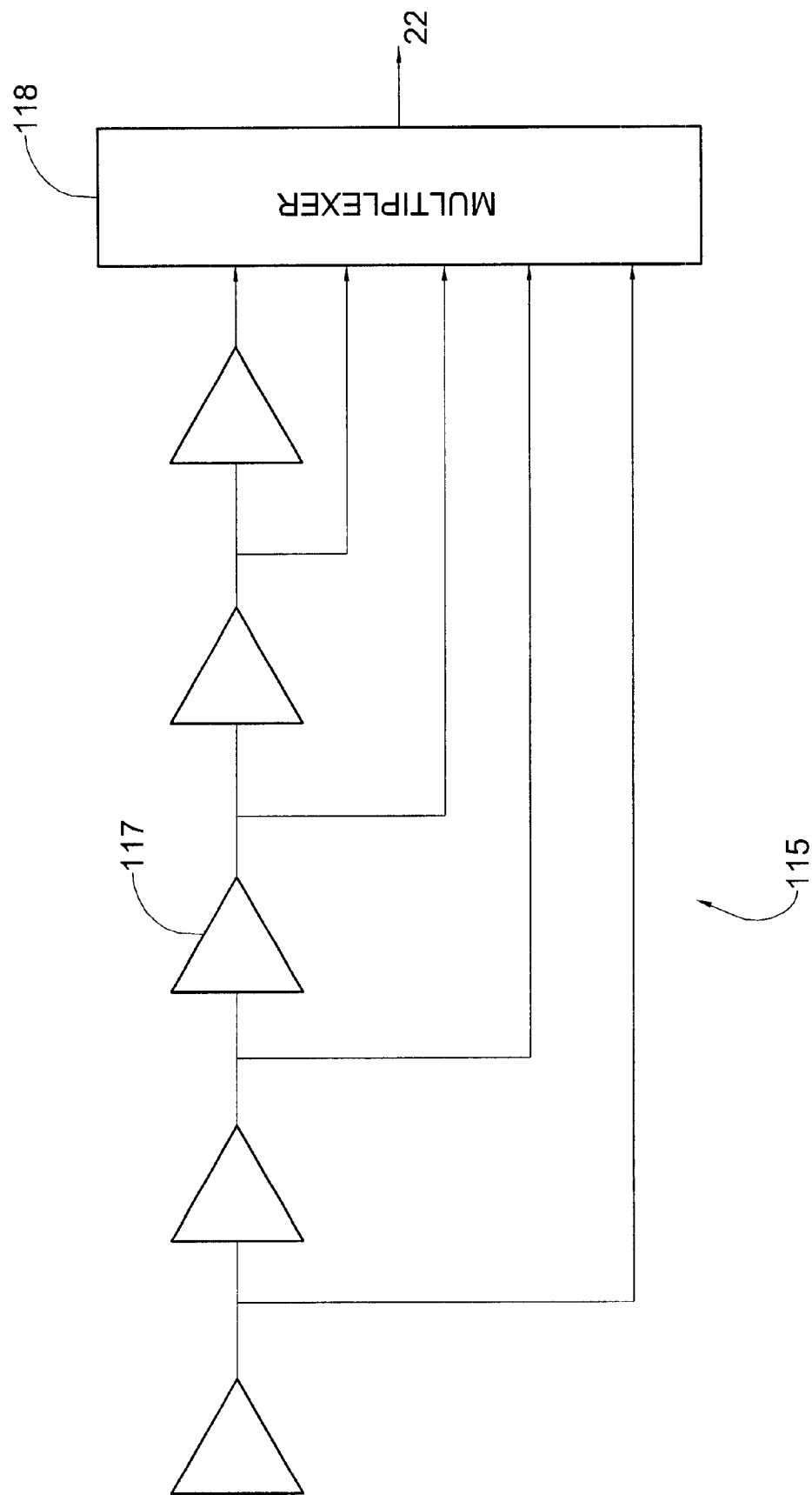
FIG. 11 shows schematically a calibration circuit for compensating for delays in the threshold discriminator shown in FIG. 3.

FIG. 11 shows schematically a calibration circuit 115 that may be connected between each threshold discriminator 102 and the corresponding monostable 25 (shown in FIG. 3) for fine adjustment of propagation delays in the threshold discriminator, which is apt to vary from channel to channel owing to process parameter variation. It will be understood that all of the threshold discriminators must be subject to identical delays, since otherwise they will reach their respective peak values at different times notwithstanding that their respective signals are initiated at identical time origins. This, of course, must be avoided since otherwise the whole object in avoiding, or compensating for, time-walk is rendered moot.

The calibration circuit 115 comprises a series of delay circuits 117 connected in cascade and each coupled to a respective input of a multi-pole switch 118 having a single output connected to the monostable 25. In use, a corresponding calibration circuit 115 is connected to the output of the respective threshold discriminator 24 connected to each pixel 12 in the detector 11 and a signal is applied to each of the pixels simultaneously. This should give rise to each of the monstables 25 producing a signal simultaneously. However, in practice, this is not the case owing to the different delays of the threshold discriminators 102, as explained above. Therefore, the threshold discriminators 102 are calibrated by adjusting the switch 118, whereby different numbers of delay circuits 117 are successively serially connected between the threshold discriminator 102 and the monostable 22, thus changing the effective overall delay. This is done for different settings of the switch 118, until each of the monostables 22 produces an output at the same time. The respective switches 116 are then left intact or, if desired, they may be removed and the requisite number of delay circuits 118 may be hard-wired between the between the respective threshold discriminator 102 and the corresponding monostable 25.

It will be apparent that other modifications may be effected to the particular embodiments as described without departing from the spirit of the invention.

Thus, for example, whilst the invention has been described with particular regard to the detection of γ-ray emissions, it is to be understood that the same principles are equally well applicable for the detection of other high-energy particles. As will further be appreciated, such high-energy particles may be photons or charged particles.

Likewise, although the use of the multi-pixel sensors within a PET nuclear imaging system has been described, it is to be understood that the same principles are equally well suited for use with SPECT and Compton cameras.

It should also be pointed out that while the sensor modules as described are based on scintillators and photomultiplier tubes, other semi-conductor sensors like CdTe and CdZnTe may also be employed in which case the pixels are high resistive elements.

Additionally, it is possible to remove the SR Flip Flop 65 in the ASIC if the sensor modules are applied to SPECT. This part is used to shut down the clock signal 60, which is important for determination of the simultaneity. However the apparatus like SPECT or Anger Camera do not need it.

What is claimed is:

1. A method for detecting an active pixel in a sensor segment having a plurality of addressable pixels, the method comprising the steps of:
    (a) for each trigger event that causes a pixel to go active, setting a corresponding resettable latch from an initial unset logic state to a set logic state and establishing a time window during which another pixel which becomes active in said sensor is assumed to originate from said trigger event,
    (b) for all pixels that become active within said time window:
        i) sampling and holding a corresponding analog value of the pixel in response to a logic signal indicative of another pixel currently being active,
        ii) establishing an incident time of the pixel going active,
        iii) sparsely reading each of the latches in said segment so as successively to identify latches which are in said set logic state each corresponding to an active pixel having a known address in said segment,
        iv) for each active pixel associating the known address thereof with the incident time of the pixel going active and the respective sampled and held analog value,
        v) repeating steps iii) and iv) in respect of successive active pixels, and
        vi) resetting said latches.

2. The method according to claim 1, for determining a respective energy value and incident time of an active pixel in a first detector segment of the sensor, wherein the sensor contains at least one other detector segment having therein an active pixel that causes the logic signal indicative of another pixel currently being active to be set.

3. The method according to claim 2, being performed for each detector segment in the sensor so as to determine a respective energy value and incident time of an active pixel in each detector segment of the sensor containing pixels that are active simultaneously.

4. The method according to claim 1, further including:
    (c) determining a cumulative energy value associated with multiple active pixels in each of said detector segments so as identify active pixels that are produced by Compton scattering.

5. The method according to claim 1, further including detecting an "active" pixel by threshold discriminating an accumulated charge signal produced by the pixel going "active" by:

(d) shaping the accumulated charge signal with a filter prior to effecting threshold discrimination thereof, and (e) limiting a slew rate of the filter so that the filtered accumulated charge signal reaches a predetermined threshold at a time that remains constant irrespective both of an amplitude of said signal and of charge collection time.

6. The method according to claim 5, wherein the filter includes an amplifier and step (e) includes limiting an output current of the amplifier so as to limit a rate at which charge is collected at an output thereof.

7. The method according to claim 6, wherein said step of limiting the output current of the amplifier includes limiting the current available in an output of the amplifier for limiting a maximum sink and/or source current thereof.

8. Use of the method according to claim 1 in a simultaneity detection positron emission computer tomography (PET) system that performs imaging by simultaneously detecting a pair of photons emitted at an angle of 180° upon mutual annihilation of a positron and an electron.

9. The method according to claim 1, further including:

(f) setting active the logic signal indicative of another pixel currently being active so as to determine the energy and incident time of a single active pixel in the sensor.

10. The method to claim 1, further including:

(g) providing an initiation signal when the active pixel is detected, and (h) measuring the respective analog value of the active pixel at a predetermined time interval $t_D$ after said initiation.

11. The method according to claim 10, including the steps of:

(i) for each pixel providing a fast shaper having a fast time constant for shaping a charge signal associated with the pixel so as to generate a fast response curve which quickly rises above a predetermined threshold, (j) simultaneously shaping the charge signal via a slow shaper having a slow time constant so as to generate a slow response curve having high signal to noise ratio, (k) determining a time delay $\Delta t$ for the fast response curve to exceed said predetermined threshold, and (l) sampling the slow response curve at a further time interval $t_p - \Delta t$ where $t_p$ is the time at which the slow response curve reaches its peak value so as to sample the slow response curve substantially at its peak value.

12. The method according to claim 11, further including:

(m) limiting a slew rate of the fast shaper so that an output thereof reaches a predetermined threshold at an initiation time $T_o$ that remains constant irrespective both of an amplitude of the data signal and of charge collection time.

13. The method according to claim 1, wherein step (b) includes:

i) providing a lookup table having a plurality of addressable locations each corresponding to a respective pixel in the sensor and storing the known address of the respective pixel, ii) using each set latch in turn to point to a corresponding addressable location in said lookup table so as to read the known address of the corresponding active pixel, and iii) using each set latch in turn to address a corresponding channel of an analog multiplexer carrying the corresponding sampled and held value of the respective active pixel.

14. A simultaneity detector for detecting simultaneously active pixels in a sensor having at least two addressable segments each containing a plurality of addressable pixels, the simultaneity detector comprising:

a respective sample and hold unit coupled to each pixel in each of the segments, each for sampling and holding a corresponding analog value associated with the pixel, a respective resettable latch coupled to each of the sample and hold units for changing from an initial unset logic state to a set logic state when the corresponding pixel goes active thereby establishing a time window within which any other pixel that subsequently goes active is considered to be a simultaneously active pixel, a logic circuit coupled to all segments in the detector for detecting two simultaneous segments in each of which there exists at least one active pixel, a lookup table in each segment having a plurality of addressable locations each corresponding to a respective pixel in the respective segment and storing the known address of the respective pixel, an analog multiplexer in each segment having a plurality of addressable channels each coupled to a respective sample and hold unit in said segment for carrying the corresponding sampled and held value of the respective pixel, a sparse readout circuit in each segment coupled to each of the latches in the respective segment for sparsely reading each of the latches therein so as successively to identify latches which are in said set logic state each corresponding to an active pixel having a known address in the respective segment, said sparse readout circuit being responsive to each of the set latches in turn for pointing successively to an addressable location in said lookup table so as to read the known address of the corresponding active pixel, and for addressing a corresponding channel of the analog multiplexer so as to derive the respective analog value of the corresponding active pixel, and a reset unit coupled to each of the latches in the respective segment for resetting said latches at a termination of said time window or within said time window if no simultaneous segments are detected.

15. The simultaneity detector according to claim 14, wherein each sample and hold unit includes:

a fast shaper having a fast time constant coupled to the respective pixel for producing a timing pulse by fast shaping an output from said pixel, the timing pulse having a known relationship to an incident time of the respective pixel going active, a slow shaper having a slow time constant coupled to the respective pixel for simultaneously shaping the charge signal associated with the respective pixel so as to generate a slow response curve having high signal to noise ratio, a threshold discriminator for determining a time delay $\Delta t$ for the fast response curve to exceed said predetermined threshold, and a sampling circuit for sampling the slow response curve at a further time interval $t_p - \Delta t$ where $t_p$ is the time at which the slow response curve reaches its peak value so as to sample the slow response curve substantially at its peak value.

16. The simultaneity detector according to claim 15, wherein each sample and hold unit further includes:

a preamplifier connected to the respective pixel for amplifying electrical charge derived from an electrical pulse produced thereby when being struck by radiation;

said fast and slow shapers begin coupled to an output of the preamplifier.

17. The simultaneity detector according to claim 15, further including:

a slew rate limiter coupled to an output of the threshold discriminator for limiting a slew rate of the fast shaper so that an output signal thereof reaches a predetermined threshold at a time that remains constant irrespective both of an amplitude of said output signal and of charge collection time.

18. The simultaneity detector according to claim 17, wherein the fast shaper an amplifier and the slew rate limiter is adapted to limit an output current of the amplifier so as to limit a rate at which charge is collected at an output thereof.

19. The simultaneity detector according to claim 18, including a current limiter for limiting the current available in an output of the amplifier for limiting a maximum sink and/or source current thereof.

20. The simultaneity detector according to claim 19, further including:

a respective calibration circuit connected to an output of each threshold discriminator for fine adjustment of varying propagation delays in the threshold discriminators owing to process parameter variation.

21. The simultaneity detector according to claim 20, wherein each calibration circuit includes:

a series of delay circuits connected in cascade and each having a respective output coupled to a respective input of a multi-pole switch having an output that is fed to the respective slew rate limiter.

22. The simultaneity detector according to claim 14, further including:

an energy summer for determining a cumulative energy value associated with two or more active pixels in each of said segments and discarding information relating thereto if said cumulative energy value is not indicative of Compton scattering.

23. A positron emission computer tomography (PET) nuclear imaging system that performs imaging by simultaneously detecting a pair of photons emitted at an angle of 180° caused by mutual annihilation of a positron and an electron, including the simultaneity detector according to claim 14.

24. A method for reading an analog data signal derived from an accumulated charge emitted by an active pixel in a sensor having a plurality of addressable pixels, the method comprising the steps of:

(a) converting the analog data signal associated with the active pixel to a digital signal having a first logic state and converting corresponding analog data signals associated with inactive pixels in the sensor to corresponding digital signals each having a second opposite logic state, (b) using said digital signals to identify the active pixel, and (c) reading a magnitude of the analog data signal in respect of said active pixel, (d) providing an initiation signal when the data signal is emitted by the active pixel, (e) measuring the magnitude of the data signal at a predetermined time interval $t_D$ after said initiation signal so as to read the magnitude of the data signal, and (f) integrating the charge in order to generate said initiation signal whose magnitude is proportional to the accumulated charge.

25. The method according to claim 24, further including:

(g) shaping the accumulated charge signal with a filter prior to effecting threshold discrimination thereof, and (b) limiting a slew rate of the filter so that the filtered accumulated charge signal reaches a predetermined threshold at a time that remains constant irrespective both of an amplitude of said signal and of charge collection time.

26. The method according to claim 25, wherein the filter includes an amplifier and step (e) includes limiting an output current of the amplifier so as to limit a rate at which charge is collected at an output thereof.

27. The method according to claim 26, wherein said step of limiting the output current of the amplifier includes limiting the current available in an output of the amplifier for limiting a maximum sink and/or source current thereof.

28. A positron emission computer tomography (PET) nuclear medicine apparatus comprising:

a detector including a plurality of pixels for producing charge signals on being hit by γ-rays, a respective initiation detector coupled to each pixel, for detecting the initiation of the γ-ray emission, a respective address detector coupled to each pixel, for detecting the address of the pixel producing the charge signals on being hit by γ-rays, a readout circuit for reading out the address signal and the energy signal from the pixel producing the charge signals on being hit by γ-rays, a coincidence detector for detecting coincidence of emission of two or more pixels, a constructing unit for constructing an image based on output signals of the readout circuit, and a counter for counting a number of pixels producing charge signals on being hit by γ-rays.

29. The positron emission computer tomography (PET) nuclear medicine apparatus according to claim 28, further comprising:

a reset circuit for resetting the readout circuit at least in the case the counter counts more pixels than a predetermined number or the coincidence detector does not detect a coincidence.

* * * * *

UNITED STATES PATENT AND TRADEMARK OFFICE
CERTIFICATE OF CORRECTION

PATENT NO.    : 6,590,215 B2
DATED         : July 8, 2003
INVENTOR(S)   : Nygard et al.

It is certified that error appears in the above-identified patent and that said Letters Patent is hereby corrected as shown below:

Column 20,
Line 16, "(b)" change to -- (h) --;
Line 35, after "γ-ray emission," insert paragraph -- a respective energy detector coupled to each pixel for detecting the energy of the γ-ray emission, --.

Signed and Sealed this

Sixth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO.    : 6,590,215 B2
DATED         : July 8, 2003
INVENTOR(S)   : Elmar Nygard et al.

It is certified that error appears in the above-identified patent and that said Letters Patent is hereby corrected as shown below:

Title page,
Item [73], Assignee, change as follows:

-- [73] Assignee: IDEAS ASA, Hovik (NO);
                Toshiba Corporation, Tokyo (JP) --

Signed and Sealed this

Twenty-eighth Day of December, 2004

JON W. DUDAS
*Director of the United States Patent and Trademark Office*